(12) United States Patent
Li et al.

(10) Patent No.: US 12,194,004 B2
(45) Date of Patent: Jan. 14, 2025

(54) NANO-DELIVERY CARRIER FOR TARGETED TUMOR ADMINISTRATION AND APPLICATION THEREOF

(71) Applicant: Guizhou Provincial People's Hospital, Guiyang (CN)

(72) Inventors: Yaying Li, Guiyang (CN); Lin Liu, Guiyang (CN); Bin Yang, Guiyang (CN); Zhenhua Luo, Guiyang (CN)

(73) Assignee: Guizhou Provincial People's Hospital, Guiyang (CN)

( * ) Notice: Subject to any disclaimer, the term of this patent is extended or adjusted under 35 U.S.C. 154(b) by 0 days.

(21) Appl. No.: 18/788,060

(22) Filed: Jul. 29, 2024

(65) Prior Publication Data
US 2024/0408036 A1    Dec. 12, 2024

Related U.S. Application Data

(63) Continuation of application No. PCT/CN2024/098764, filed on Jun. 12, 2024.

(30) Foreign Application Priority Data

Jun. 12, 2023 (CN) .......................... 202310693812.8

(51) Int. Cl.
| | |
|---|---|
| *A61K 31/05* | (2006.01) |
| *A61K 9/51* | (2006.01) |
| *A61K 41/00* | (2020.01) |
| *A61K 47/54* | (2017.01) |
| *A61K 47/60* | (2017.01) |
| *A61K 47/69* | (2017.01) |
| *A61P 35/00* | (2006.01) |

(52) U.S. Cl.
CPC ............ *A61K 31/05* (2013.01); *A61K 9/5115* (2013.01); *A61K 9/5123* (2013.01); *A61K 41/00* (2013.01); *A61K 47/548* (2017.08); *A61K 47/549* (2017.08); *A61K 47/60* (2017.08); *A61K 47/6923* (2017.08); *A61P 35/00* (2018.01)

(58) Field of Classification Search
CPC ...... A61K 31/05; A61K 41/00; A61K 47/548; A61K 47/549; A61K 47/60; A61K 47/6923; A61P 35/00
See application file for complete search history.

(56) References Cited

PUBLICATIONS

Xueqi Li et al., "Nanostructure of Functional Larotaxel Liposomes Decorated with Guanine-Rich Quadruplex Nucleotide-Lipid Derivative for Treatment of Resistant Breast Cancer", "Small", Jan. 31, 2021, pp. 1-11, vol. 17, Document No. 2007391.
Li Qiaolin, "Study of IR820@PEG-SPIO in Diagnosis and Laparoscopic-Assisted Photothermal Ablation in Micro Liver Cancer", "Chinese Doctoral Dissertation Full Text Database, Journal of Medical and Health Technology", Jun. 15, 2021, pp. E072-E189.

*Primary Examiner* — Robert S Cabral

(57) ABSTRACT

A nano-delivery carrier for targeted tumor administration and an application thereof are provided, which relate to the technical field of targeted anti-tumor dugs. A preparation method of the nano-delivery carrier for targeted tumor administration includes: mixing a NucA targeting a tumor and DSPE-PEG2000-NHS with DMF to obtain a mixture, adding triethylamine into the mixture, adjusting a pH of the mixture added with the triethylamine to 8-9 to react at room temperature, to thereby obtain the nano-delivery carrier for targeted tumor administration. An anti-tumor drug based on the nano-delivery carrier can correctly target to the tumor to be killed, for example, an anti-tumor drug based on the nano-delivery carrier and including RVT can target and kill ovarian cancer cells without damaging normal tissues.

5 Claims, 7 Drawing Sheets

Specification includes a Sequence Listing.

NANO-DELIVERY CARRIER FOR TARGETED TUMOR ADMINISTRATION AND APPLICATION THEREOF

TECHNICAL FIELD

The disclosure relates to the technical field of targeted tumor dugs, and more particularly to a nano-delivery carrier for targeted tumor administration and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 24046THXT-USP1-SL.xml. The XML file is 1,861 bytes; is created on Jul. 10, 2024; and is being submitted electronically via patent center.

BACKGROUND

Cancer is a major disease that currently threatens human life and health. Currently, the main treatments for tumors are surgery, chemotherapy, and radiotherapy. Patients in the middle and late stages have lost an opportunity for surgery, and although surgery can remove primary lesions, it cannot fundamentally prevent reproduction of cancer cells. The cancer is very likely to recur after surgery. Currently, a commonly used method is surgery combined with drug therapy, and the drug therapy generally uses chemotherapy. Although the chemotherapy can kill the cancer cells, it also damages a large number of normal tissue cells, and has obvious toxic and side effects, including body weakness, loss of appetite, hair loss, inhibition of hematopoietic function, damage to liver, kidney and ovarian function, induction of gastrointestinal reactions, bone marrow suppression, and liver, kidney, and heart function damage.

A targeted drug refers to a drug or its preparation that are endowed with a targeting capability. A purpose of the targeted drug is to enable the drug or its carrier to target a specific lesion site and accumulate or release an active ingredient at a target site. Using the targeted drug in the treatment of the cancer can reduce or even prevent damage to body tissues other than tumors.

Therefore, it is of great significance to develop a carrier or a drug for targeted tumor administration.

SUMMARY

Aiming at the above problems, a purpose of the disclosure is to provide a nano-delivery carrier for targeted tumor administration and an application thereof. The nano-delivery carrier for targeted tumor administration is composed of a nucleic acid aptamer (NucA) specifically targeting a tumor connected to 1,2-distearoyl-sn-glycero-3-phosphoethanolamine-N-[succinimidyl (polyethylene glycol)-2000] (DSPE-PEG2000-NHS). Based on the nano-delivery carrier for targeted tumor administration, a solvent replacement method can be used to replace N-hydroxy succinimide (NHS) with an anti-tumor active ingredient to prepare a targeted anti-tumor drug.

In order to achieve the above purpose, the disclosure can use the following technical solutions.

On the one hand, the disclosure provides a nano-delivery carrier for targeted tumor administration, and the nano-delivery carrier for targeted tumor administration is prepared by: mixing a NucA targeting a tumor and DSPE-PEG2000-NHS with N,N-dimethylformamide (DMF) to obtain a mixture, adding triethylamine into the mixture, adjusting a power of hydrogen (pH) of the mixture added with the triethylamine to 8-9 to react at room temperature, to thereby obtain the nano-delivery carrier for targeted tumor administration.

On the other hand, the disclosure provides a targeted anti-tumor drug, and the targeted anti-tumor drug is prepared by: mixing oleic acid-coated super paramagnetic iron oxide (SPIO) nanoparticles, an anti-tumor active ingredient and the nano-delivery carrier for targeted tumor administration with chloroform to obtain a mixed solution; adding ethylene glycol into the mixed solution under an ultrasonic environment; removing chloroform from the mixed solution added with the ethylene glycol to obtain a first removed solution, adding water into the first removed solution, and removing the ethylene glycol from the first removed solution added with the water to obtain a second removed solution; and performing ultrasound and centrifugation on the second removed solution to remove precipitate from the second removed solution to thereby obtain the targeted anti-tumor drug.

Still on the other hand, the disclosure provides a preparation for treating the tumor, including the targeted anti-tumor drug described above and a pharmaceutically acceptable carrier.

Beneficial effects of the disclosure at least include the follows: the anti-tumor drug based on the nano-delivery carrier for targeted tumor administration provided by the disclosure can target the tumor to be killed. For example, the anti-tumor drug containing the resveratrol based on the nano-delivery carrier can target and kill ovarian cancer cells without damaging normal tissues.

DETAILED DESCRIPTION OF EMBODIMENTS

Figure 1:
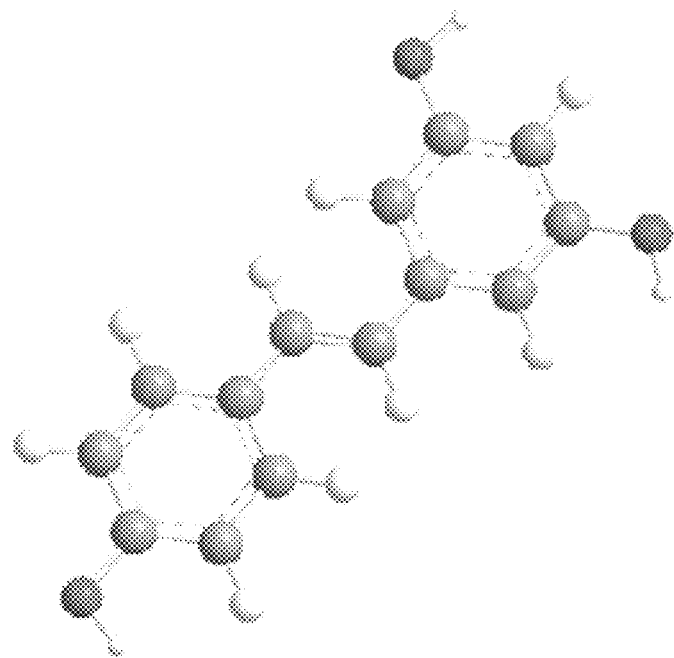
FIG. 1 illustrates a two-dimensional schematic structural diagram of resveratrol (RVT) according to an embodiment of the disclosure.

Embodiments are provided to better describe the disclosure, but a content of the disclosure is not limited to the embodiments. Therefore, those skilled in the art may make non-essential improvements and adjustments to an implementation scheme according to the above summary, which still fall within a scope of protection of the disclosure.

Terms used herein are only used to describe specific embodiments and are not intended to limit the disclosure. Unless the context has a significantly different meaning, expressions in the singular include expressions in the plural. As used herein, it should be understood that terms such as "including", "having", "containing" and the like are intended to indicate presence of features, numbers, operations, materials or combinations. The terms of the disclosure are disclosed in the specification, and are not intended to exclude a possibility that one or more other features, numbers, operations, materials or combinations thereof may exist or may be added. As used herein, "/" may be interpreted as "and" or "or", which depends on the actual situations.

An embodiment of the disclosure provides a nano-delivery carrier for targeted tumor administration, and the nano-delivery carrier for targeted tumor administration is prepared by the follows: a NucA targeting a tumor and DSPE-PEG2000-NHS are mixed with DMF to obtain a mixture, and triethylamine is added into the mixture. A pH of the mixture added with the triethylamine is adjusted to 8-9 to react at room temperature to obtain the nano-delivery carrier for targeted tumor administration.

It should be noted that the above nano-delivery carrier for targeted tumor administration connects the NucA specifically targeting the tumor with the DSPE-PEG2000-NHS to form the nano-delivery carrier for targeted tumor administration DSPE-PEG2000-NHS-NucA. In addition, during preparing the nano-delivery carrier for targeted tumor administration, UV spectrum and Fourier transform infrared spectroscopy (FTIR) can be used to determine whether the NucA is successfully connected with the DSPE-PEG2000-NHS.

In some embodiments, a molar ratio between the NucA and the DSPE-PEG2000-NHS is 1:(2.5-3.5), such as: 1:2.8, 1:3, or 1:3.2. Specifically, the molar ratio between the NucA and the DSPE-PEG2000-NHS is 1:3, and the nano-delivery carrier for targeted tumor administration prepared under this molar ratio (i.e., 1:3) has the optimal performance.

In some embodiments, the above tumor is ovarian cancer. It should be noted that the above tumor can be a tumor known in the art, such as breast cancer, lung cancer, gastric cancer, liver cancer, colorectal cancer, or ovarian cancer. When different tumors are selected, different NucAs need to be selected.

In some embodiments, when the above tumor is the ovarian cancer, the nucleotide sequence of the NucA is as shown in SEQ ID NO: 1, and the nucleotide sequence is 5'-GGTGGTGGTGGTTGTGGTGGTGGTGG-3'. It should be noted that 3' hydroxyl end is modified with an amino group (i.e., 3ammc7-r), and the amino group can react and connect with some groups, such as a carboxyl group (—COOH) and —NHS. The amino group is modified and can also modify other groups.

In some embodiments, a time for the react at room temperature can be 24 hours (h). Apparently, the reaction time can be adjusted according to specific situations, as long as the above nano delivery carrier can be prepared, for example, the reaction time can be 5 h, 10 h, 15 h or 20 h.

In some embodiments, after the preparation of the nano-delivery carrier for targeted tumor administration is completed, the nano-delivery carrier for targeted tumor administration can be dialyzed for 24 h with a dialysis membrane (a molecular weight is 3.5 kilo Dalton abbreviated as kD) to remove unreacted NucA, DSPE-PEG2000-NHS and other organic solvents.

Another embodiment of the disclosure provides a targeted anti-tumor drug, and a preparation method of the targeted anti-tumor drug includes the follows: oleic acid-coated SPIO nanoparticles, an anti-tumor active ingredient and the above nano-delivery carrier for targeted tumor administration are mixed with chloroform to obtain a mixed solution. Ethylene glycol is gradually added into the mixed solution under an ultrasonic environment. The chloroform is removed from the mixed solution added with the ethylene glycol to obtain a first removed solution. Water is added into the first removed solution. The ethylene glycol is removed from the first removed solution added with the water to obtain a second removed solution. Ultrasound and centrifugation are performed on the second removed solution to remove precipitate from the second removed solution to thereby obtain the targeted anti-tumor drug.

It should be noted that the above preparation method of the targeted anti-tumor drug is based on a solvent replacement method, which is to replace the original solution with solutions of gradually increasing polarity twice to prepare DSPE-PEG2000-RVT-NucA nanoparticles.

It should be further noted that in the above preparation method of the targeted anti-tumor drug, the terms "ultrasound", "centrifugation" and the like have the conventional meanings in the art and have no specific meanings. In addition, in some embodiments, a centrifugation condition can be 5000 revolutions per minute (rpm), and an ultrasonic power can be 60 watts (W).

In some embodiments, the above anti-tumor active ingredient is resveratrol. Specifically, a two-dimensional schematic structural diagram of the resveratrol is shown in FIG. 1, and a chemical structure of the resveratrol is shown as follows:

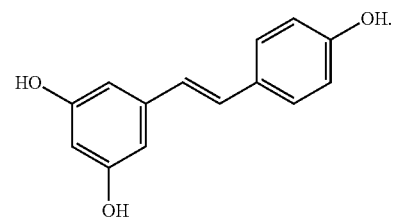 [SMILES: Oc1ccc(/C=C/c2cc(O)cc(O)c2)cc1]

It should be noted that the resveratrol (3,4',5-trihydroxy-trans-stilbene) is a natural anti-tumor active ingredient extracted from plants, which can inhibit the occurrence and development of the tumors, especially the ovarian cancer. There are no reports on applications of a novel nano encapsulated drug formulation of the resveratrol in the ovarian cancer based on a diversity of chemical properties of the resveratrol binding with ovarian cancer-related proteins. In the nano-delivery carrier for targeted tumor administration of the disclosure, a trans isomer of the resveratrol is retained, which ensures the specificity and stability of the binding of the resveratrol to the target site, thereby exerting an anti-cancer sensitization effect. With the help of a molecular imaging method, through a killing experiment (also referred to as cytotoxicity test) of ovarian cancer cells, acquisition of live biological information of for integration of diagnosis and treatment of the ovarian cancer by retaining the physical and chemical characteristics of natural drugs is achieved.

In some embodiments, a weight ratio of the oleic acid-coated SPIO nanoparticles:the anti-tumor active ingredient: the nano-delivery carrier for targeted tumor administration is (4.5-5.5):(0.5-1.5):(9.5-10.5), for example, 4.7:0.8:9.7, 5:1:10, or 5.3:1.3:10.3. Specifically, the weight ratio is 5:1:10.

In some embodiments, an addition amount of the ethylene glycol is 3-5 times volume of the mixed solution, for example, 4 times.

It should be further noted that the above oleic acid-coated SPIO nanoparticles can be prepared by methods known in the art. For example, an oleic acid iron complex is first prepared by a known method, and then the oleic acid iron complex is coated with oleic acid to obtain the oleic acid-coated SPIO nanoparticles.

In some embodiments, a preparation method of the oleic acid-coated SPIO nanoparticles includes the following steps (1)-(2).

(1) Synthesis of the oleic acid iron complex, specifically includes the follows: ferric chloride hexahydrate ($FeCl_3 \cdot 6H_2O$) is reacted with sodium oleate in a mixture of ethanol, distilled water and n-hexane to obtain a reacted mixture. The reacted mixture is washed with distilled water to obtain a washed mixture. The hexane is removed from the washed mixture through a rotary evaporator to obtain the oleic acid iron complex.

(2) Synthesis of the oleic acid-coated SPIO nanoparticles, specifically includes the follows: the prepared oleic acid iron complex and the oleic acid are mixed with 1-octadecene with heating 110 Celsius degrees (° C.) and evacuating for 30 minutes (min) to obtain a reactant. The reactant is slowly heated to 320° C. at a rate of 5° C. per minute with maintaining for 30 minutes under argon protection. The heated reactant is cooled to the room temperature and taken out, and the cooled reactant is washed and precipitated in chloroform to obtain the oleic acid-coated SPIO nanoparticles.

Still another embodiment of the disclosure provides a preparation for treating the tumor, including the above targeted anti-tumor drug and a pharmaceutically acceptable carrier. It should be noted that according to clinical needs, the above targeted anti-tumor drug can be added with a pharmaceutically acceptable carrier to prepare different dosage forms, such as an injection form or an oral preparation form.

In order to better understand the disclosure, the content of the disclosure is further described in conjunction with specific embodiments below, but the content of the disclosure is not only limited by the following embodiments.

Embodiment 1 Synthesis Methods of Nanomaterials (1) Synthesis of the Oleic Acid Iron Complex $FeCl_3 \cdot 6H_2O$ (2.7 grams abbreviated as g) is reacted with sodium oleate (9.125 g) in a mixture of ethanol (20 milliliters abbreviated as mL), distilled water (15 mL) and n-hexane (35 mL) at 70° C. for 4 h to obtain a reacted mixture. The reacted mixture is collected by using a separatory funnel, and is washed with distilled water (50 mL) to obtain a washed mixture. The hexane is removed from the washed mixture through the rotary evaporator to obtain the oleic acid iron complex. The oleic acid iron complex is packaged in a round bottomed flask and stored under a dry condition at the room temperature.

(2) Synthesis of the Oleic Acid-Coated SPIO Nanoparticles (OA-SPIO)

The oleic acid iron complex (1.0 g) prepared in step (1) and the oleic acid (0.25 g) are mixed with 1-octadecene (5.5 g) with heating to 110° C. and evacuating for 30 min to obtain a reactant. The reactant is slowly heated to 320° C. at a rate of 5° C. per minute with maintaining for 30 min under argon protection. The heated reactant is cooled to the room temperature and taken out, and the cooled reactant is washed and precipitated in chloroform to obtain the oleic acid-coated SPIO nanoparticles.

(3) Synthesis of DSPE-PEG2000-NHS-NucA (PEG-NucA)

The NucA and the DSPE-PEG2000-NHS are added into a DMF solution according to a molar ratio of the NucA and the DSPE-PEG2000-NHS at 1:3 to obtain a mixed solution. Triethylamine is added into the mixed solution, and a pH of the mixed solution added with the triethylamine is adjusted to 8.5 to react at room temperature for 24 h to obtain a reacted solution. The reacted solution is dialyzed with a dialysis membrane (a molecular weight is 3.5 kD) for 24 h to remove unreacted NucA, DSPE-PEG2000-NHS and other organic solvents. The UV spectrum and FTIR can be used to determine whether the NucA is successfully connected with the DSPE-PEG2000-NHS.

(4) Synthesis of DSPE-PEG2000-SPIO-RVT-NucA (PEG-SPIO-RVT-NucA) Nanoparticles

The DSPE-PEG2000-SPIO-RVT-NucA nanoparticles are prepared according to the solvent replacement method, and a specific preparation process is as follows: the OA-SPIO prepared in the step (2), the RVT and the PEG-NucA prepared in the step (3) are added in to a round necked flask containing 0.5 mL of chloroform according a weight ratio of the OA-SPIO, the RVT and the PEG-NucA at 10:2:20 to obtain a mixed solution. The mixed solution is placed in an ultrasonic cleaner to perform a brief ultrasound, so that each component in the mixed solution can be fully dissolved. An ethylene glycol solution with a volume of 4 times that of the mixed solution is gradually added into the mixed solution under the ultrasonic environment. The mixed solution added with the ethylene glycol is evaporated by the rotary evaporator to remove the chloroform to obtain a first removed solution, moderate amount of deionized water is added into the first removed solution, and an ultrafiltration centrifuge tube (100 molecular weight abbreviated as mw) is used to perform multiple centrifugations on the first removed solution to remove the ethylene glycol solution to obtain a second removed solution. A cell ultrasonic crusher is used to perform ultrasound on the second removed solution for 5 min at a power of 60 W. The solution after ultrasound is centrifuged at 5000 rpm to remove the precipitate, to thereby remove large aggregates to obtain the PEG-SPIO-RVT-NucA nanoparticles.

Synthesis methods of PEG-SPIO (i.e., the SPIO nanoparticles coated with the PEG) and PEG-SPIO-RVT (i.e., the SPIO nanoparticles and the RVT coated with the PEG) of a control group are the similar as the above.

Embodiment 2 Characterization of the Nanomaterials

Figure 2:
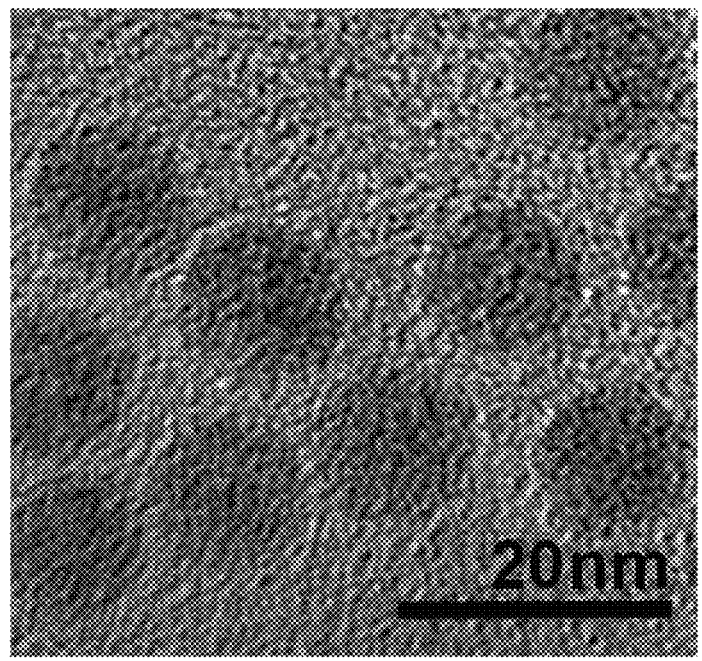
FIG. 2 illustrates a transmission electron micrograph of polyethylene glycol-super paramagnetic iron oxide (PEG-SPIO) nanoparticles prepared in an embodiment.
Figure 3:
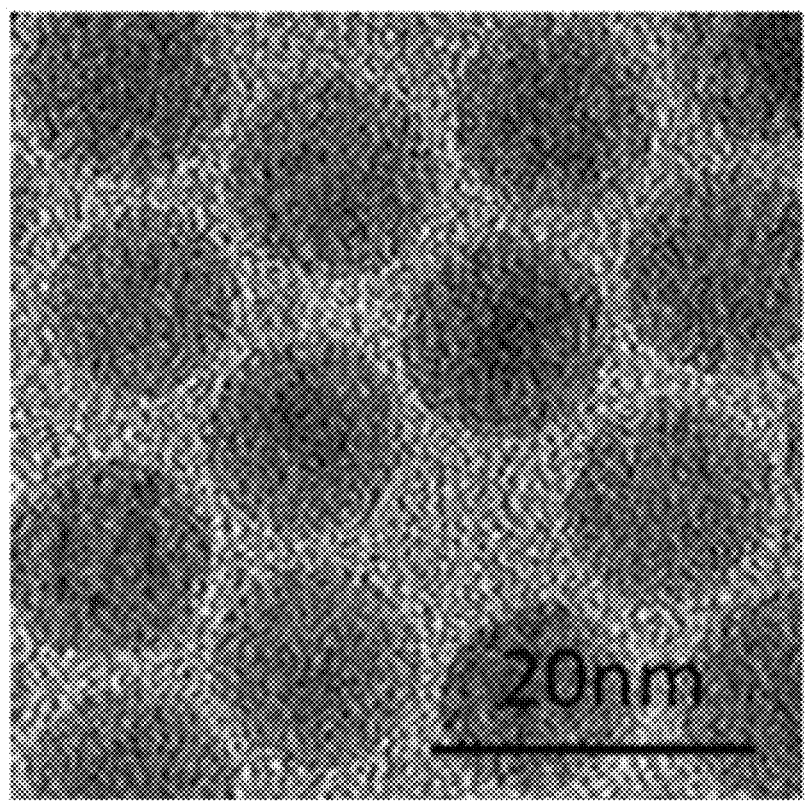
FIG. 3 illustrates a transmission electron micrograph of PEG-SPIO-RVT nanoparticles prepared in an embodiment.

The PEG-SPIO nanoparticles and the PEG-SPIO-RVT nanoparticles prepared in the embodiment 1 are analyzed by transmission electron microscopy, and the results are shown in FIG. 2 and FIG. 3.

Figure 4:
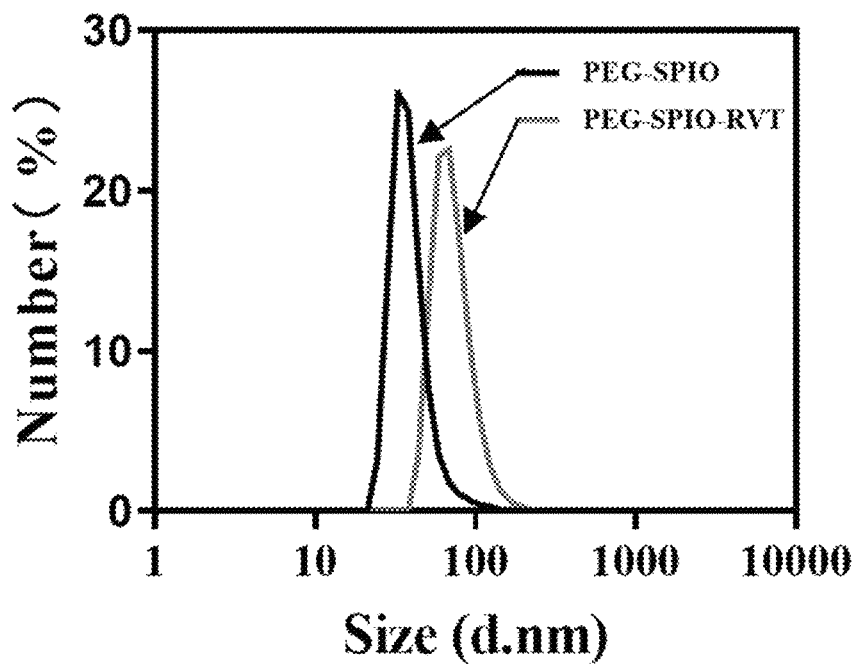
FIG. 4 illustrates a schematic diagram of a detection result of hydrated particle sizes of the PEG-SPIO nanoparticles and the PEG-SPIO-RVT nanoparticles prepared in the embodiment.

The PEG-SPIO nanoparticles and the PEG-SPIO-RVT nanoparticles prepared in the embodiment 1 are tested for hydrated particle size, and the result is shown in FIG. 4.

Figure 5:
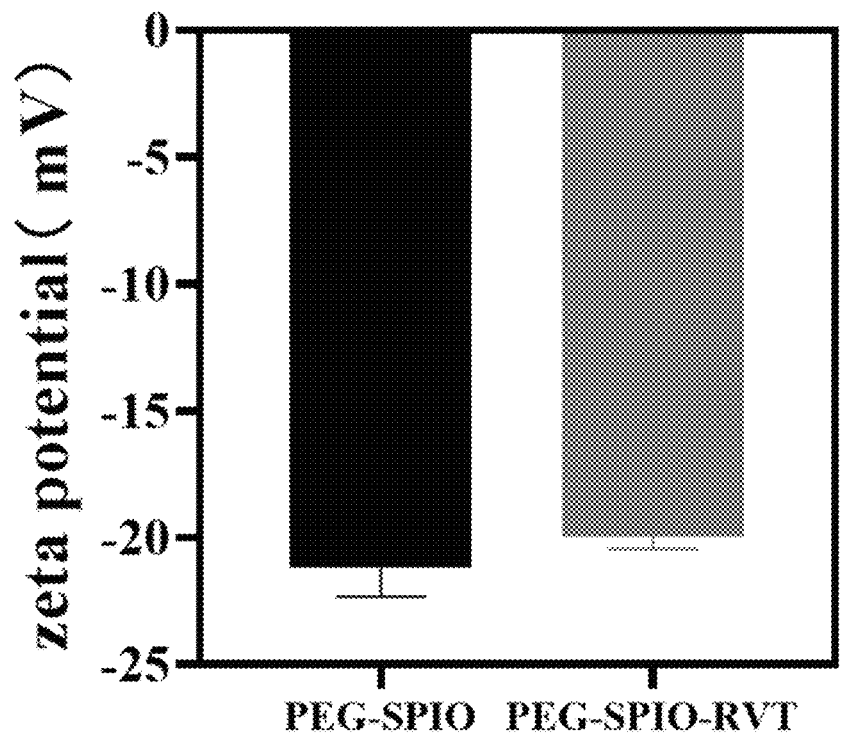
FIG. 5 illustrates a schematic diagram of zeta potential on surfaces of the PEG-SPIO nanoparticles and the PEG-SPIO-RVT nanoparticles prepared in the embodiment.

Zeta potential of surfaces of the PEG-SPIO nanoparticles and the PEG-SPIO-RVT nanoparticles prepared in the embodiment 1 is analyzed, and the result is shown in FIG. 5.

Figure 6:
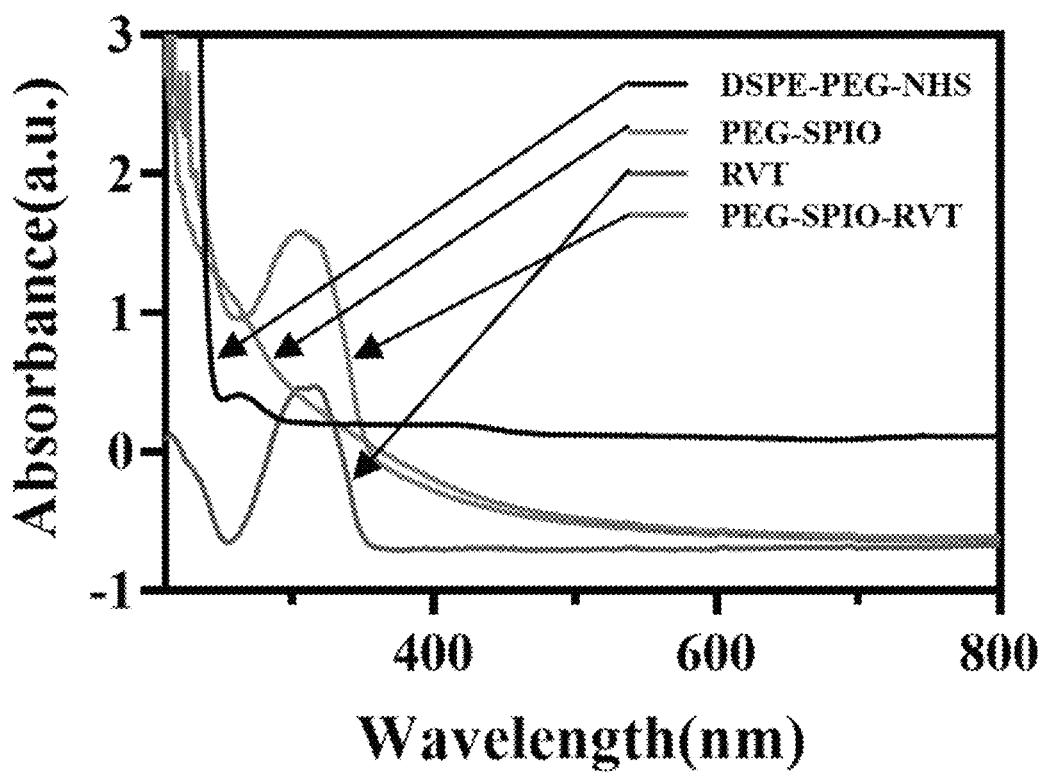
FIG. 6 illustrates an ultraviolet (UV)/visible light absorption spectrum of the PEG-SPIO nanoparticles and the PEG-SPIO-RVT nanoparticles prepared in the embodiment.

The PEG-SPIO nanoparticles and the PEG-SPIO-RVT nanoparticles prepared in the embodiment 1 are subjected to UV/visible absorption spectral analysis, and the result is shown in FIG. 6.

Figure 7:
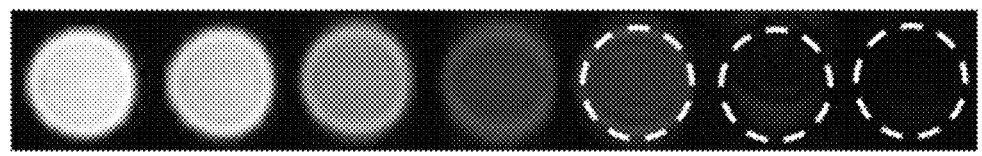
FIG. 7 illustrates a schematic diagram of in vitro magnetic resonance imaging (MRI) of the PEG-SPIO nanoparticles and the PEG-SPIO-RVT nanoparticles prepared in the embodiment with different concentrations of iron ions (i.e., different Fe concentrations).
Figure 7:
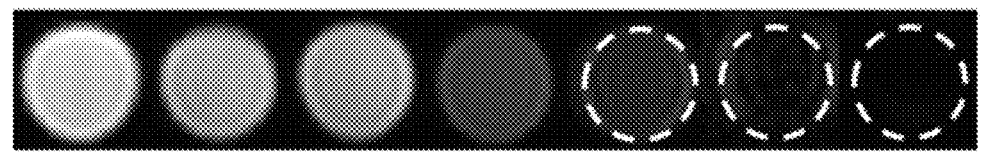
Figure 8:
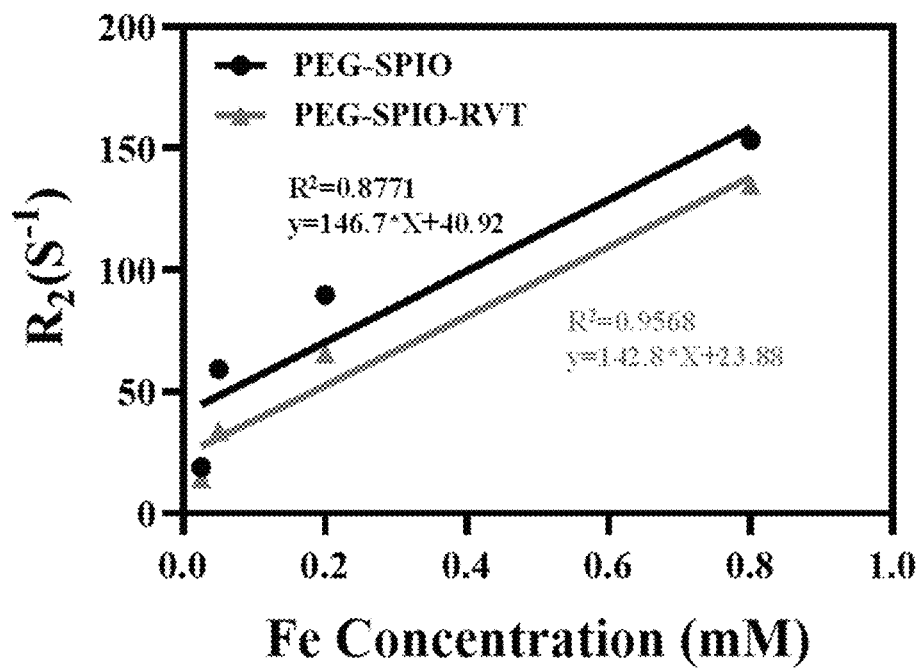
FIG. 8 illustrates a frequency diagram of the in vitro magnetic resonance imaging (MRI) of the PEG-SPIO nanoparticles and the PEG-SPIO-RVT nanoparticles prepared in the embodiment with different concentrations of iron ions.

The PEG-SPIO nanoparticles and the PEG-SPIO-RVT nanoparticles prepared in the embodiment 1 are subjected to in vitro magnetic resonance imaging analysis at different concentrations. The in vitro magnetic resonance imaging analysis graph is shown in FIG. 7, and the in vitro magnetic resonance imaging frequency diagram is shown in FIG. 8.

Embodiment 3 Cell Viability Detection

Figure 9:
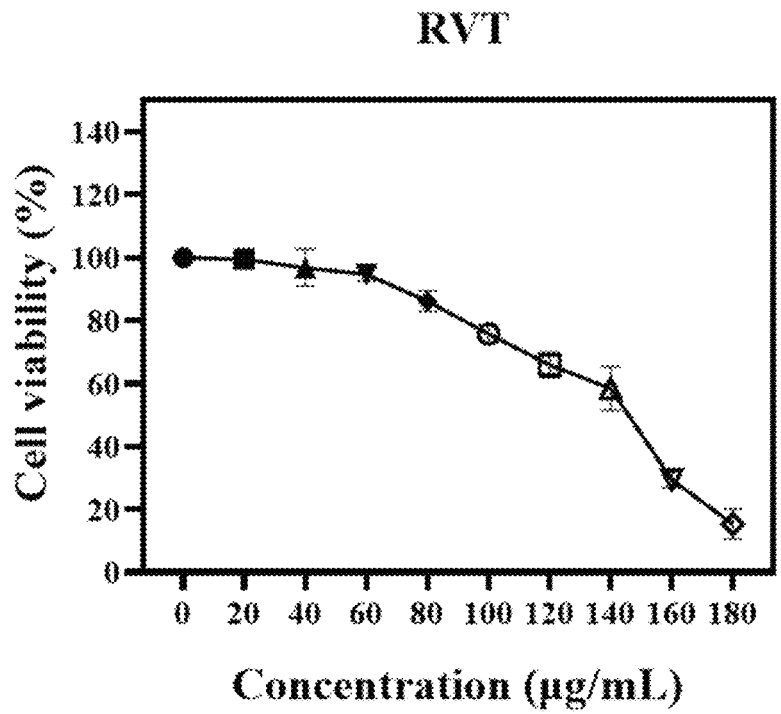
FIG. 9 illustrates a schematic diagram of a detection situation of cell viability of cells treated with RVT.

In order to verify whether RVT can cause death of the tumor cells, SKOV3 cells are treated with RVT at different concentrations for 24 h, and viability of the SKOV3 cells treated with RVT is detected by using a cell counting kit-8 (CCK-8) detection reagent. The results are shown in FIG. 9. As the RVT concentration increases, the viability of the SKOV3 cells gradually shows a downward trend.

Figure 10:
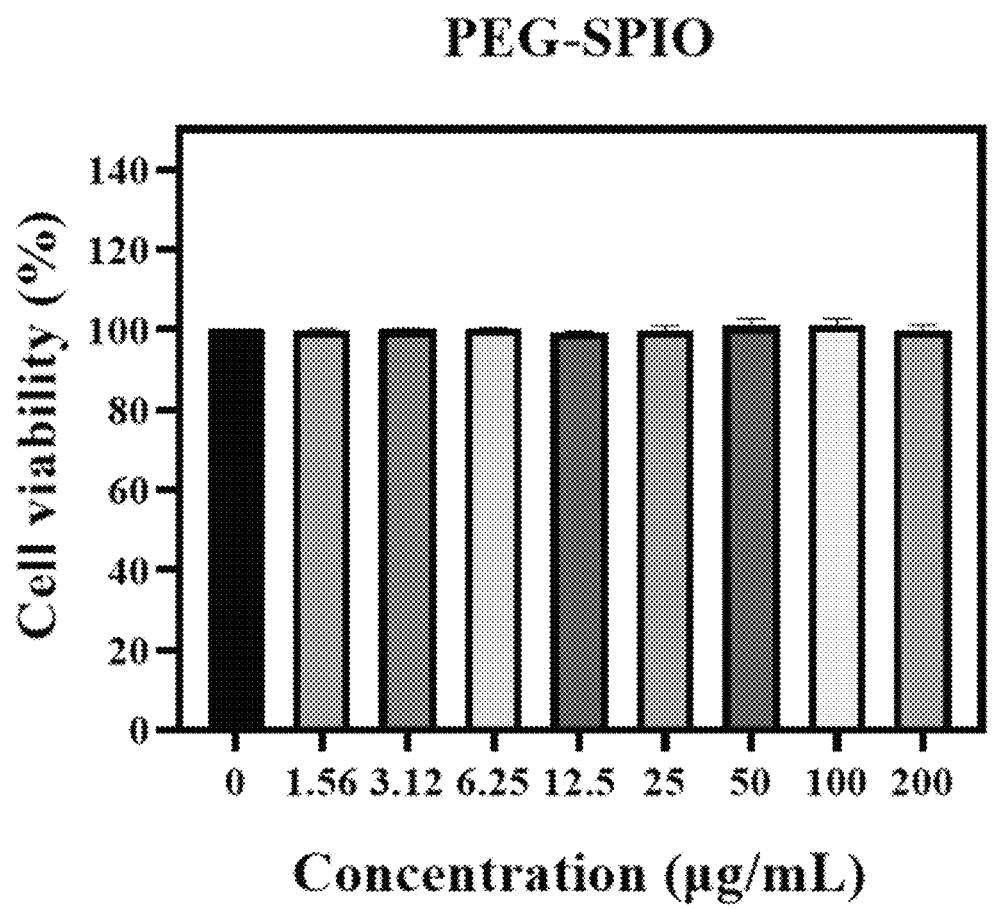
FIG. 10 illustrates a schematic diagram of a detection situation of cell viability of cells treated with PEG-SPIO.

In addition, the SKOV3 cells are treated with PEG-SPIO at different concentrations for 24 h, and the viability of the SKOV3 cells treated with PEG-SPIO is detected by using the CCK-8 detection reagent. The results are shown in FIG. 10. When the concentration of PEG-SPIO is as high as 200 micrograms per milliliter (μg/mL), it does not cause death of the SKOV3 cells, which indicates that PEG-SPIO has no obvious cytotoxicity to cells.

Figure 11:
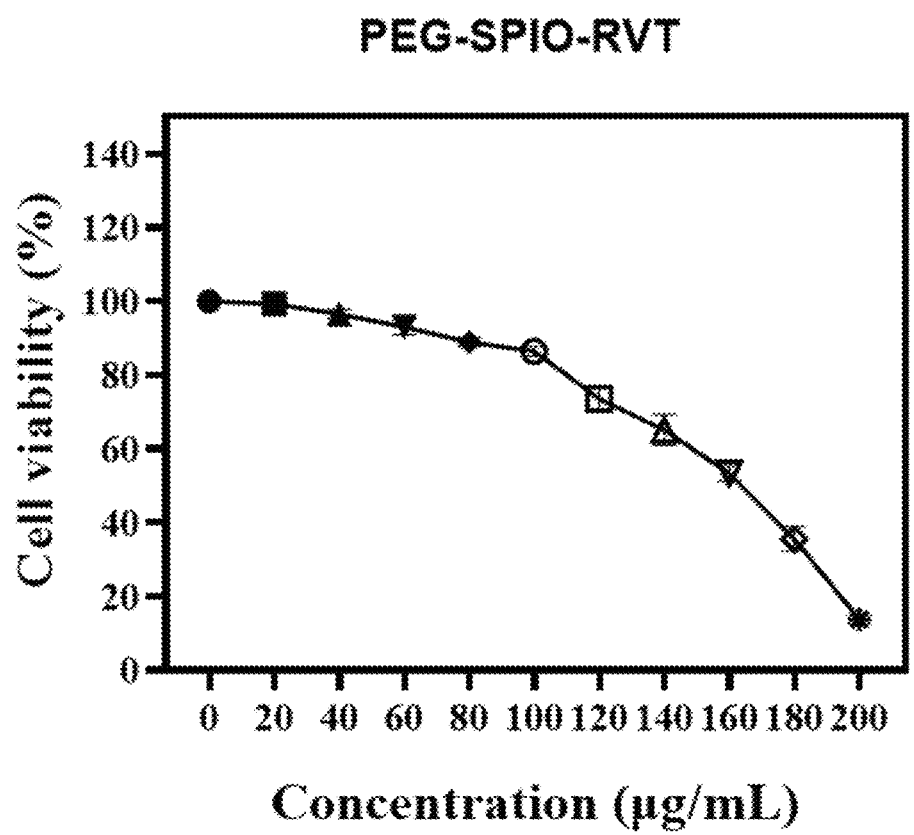
FIG. 11 illustrates a schematic diagram of a detection situation of cell viability of cells treated with the PEG-SPIO-RVT.

Furthermore, the SKOV3 cells are treated with RVT-encapsulated PEG-SPIO-RVT nanoparticles for 24 h, and the viability of the SKOV3 cells treated with RVT-encapsulated PEG-SPIO-RVT nanoparticles is detected by using the CCK-8 detection reagent. The results are shown in FIG. 11. The results are the same as that of treating with RVT alone. As the concentration of PEG-SPIO-RVT nanoparticles increases, the viability of the SKOV3 cells decreases significantly. The above results indicate that RVT is the real cause of the SKOV3 cell death.

Embodiment 4 Ovarian Cancer Tumor Cell Killing Verification

The experimental verification on ovarian cancer tumor cells in the embodiment of the disclosure shows that the natural drug targeted delivery system has a killing effect on the ovarian cancer cells without damaging normal tissues.

Finally, it should be noted that the above embodiments are merely used to describe the technical solutions of the disclosure rather than to limit it. Although the disclosure is described in detail with reference to the embodiments, those skilled in the art should understand that the technical solutions of the disclosure can be modified or replaced by equivalents without departing from the purpose and scope of the technical solutions of the disclosure, which should be covered by the scope of the claims of the disclosure.

What is claimed is:

1. A targeted anti-tumor drug, wherein the targeted anti-tumor drug is prepared by: mixing oleic acid-coated super paramagnetic iron oxide (SPIO) nanoparticles, an anti-tumor active ingredient and a nano-delivery carrier for targeted tumor administration with chloroform to obtain a mixed solution; adding ethylene glycol into the mixed solution gradually under an ultrasonic environment; removing the chloroform from the mixed solution added with the ethylene glycol to obtain a first removed solution, adding water into the first removed solution, and removing the ethylene glycol from the first removed solution added with the water to obtain a second removed solution; and performing ultrasound and centrifugation on the second removed solution to remove precipitate from the second removed solution to thereby obtain the targeted anti-tumor drug;

wherein the anti-tumor active ingredient is resveratrol;

wherein the nano-delivery carrier for targeted tumor administration is prepared by: mixing a nucleic acid adapter (NucA) targeting a tumor and 1,2-distearoyl-sn-glycero-3-phosphoethanolamine-N-[succinimidyl (polyethylene glycol)-2000] (DSPE-PEG2000-NHS) with N,N-dimethylformamide (DMF) to obtain a mixture, adding triethylamine into the mixture, adjusting a power of hydrogen (pH) of the mixture added with the triethylamine to 8-9 to react at room temperature, to thereby obtain the nano-delivery carrier for targeted tumor administration;

wherein the tumor is ovarian cancer; and the nucleotide sequence of the NucA is as shown in SEQ ID NO: 1; and wherein a molar ratio between the NucA and the DSPE-PEG2000-NHS is 1:(2.5-3.5).

2. The targeted anti-tumor drug as claimed in claim 1, wherein a weight ratio of the oleic acid-coated SPIO nanoparticles:the anti-tumor active ingredient:the nano-delivery carrier for targeted tumor administration is (4.5-5.5):(0.5-1.5):(9.5-10.5).

3. The targeted anti-tumor drug as claimed in claim 1, wherein an addition amount of the ethylene glycol is 3-5 times volume of the mixed solution.

4. A preparation for treating the tumor, comprising: the targeted anti-tumor drug as claimed in claim 1 and a pharmaceutically acceptable carrier.

5. The preparation for treating the tumor as claimed in claim 4, wherein the pharmaceutically acceptable carrier is applied to an injection form or an oral administration form.

* * * * *

```
SEQUENCE LISTING

Sequence total quantity: 1
SEQ ID NO: 1            moltype = DNA  length = 26
FEATURE                 Location/Qualifiers
source                  1..26
                        mol_type = other DNA
                        organism = synthetic construct
SEQUENCE: 1
ggtggtggtg gttgtggtgg tggtgg                                        26
```